United States Patent [19]

Jahn et al.

[11] Patent Number: 4,568,383
[45] Date of Patent: Feb. 4, 1986

[54] CYCLOHEXANE-1,3-DIONE DERIVATIVES

[75] Inventors: Dieter Jahn, Neckarhausen; Wolfgang Rohr, Wachenheim; Rainer Becker, Bad Duerkheim; Norbert Götz, Worms; Bruno Würzer, Otterstadt, all of Fed. Rep. of Germany

[73] Assignee: BASF Aktiengesellschaft, Fed. Rep. of Germany

[21] Appl. No.: 498,043

[22] Filed: May 25, 1983

Related U.S. Application Data

[63] Continuation of Ser. No. 296,584, Aug. 27, 1981, abandoned.

[30] Foreign Application Priority Data

Sep. 2, 1980 [DE] Fed. Rep. of Germany ....... 3032973

[51] Int. Cl.$^4$ ......................... A01N 33/02; C07C 83/00
[52] U.S. Cl. ......................................... 71/121; 71/106; 560/125; 564/300
[58] Field of Search .................. 564/300; 71/121, 106; 560/118

[56] References Cited

U.S. PATENT DOCUMENTS 3,950,420  4/1976  Sawaki et al. ...................... 564/300
4,249,937  2/1981  Iwataki et al. .................. 564/300 X

FOREIGN PATENT DOCUMENTS 2455238  5/1975  Fed. Rep. of Germany ...... 564/300

*Primary Examiner*—Robert V. Hines
*Attorney, Agent, or Firm*—Keil & Weinkauf

[57] ABSTRACT

Cyclohexane-1,3-dione deriatives of the general formula

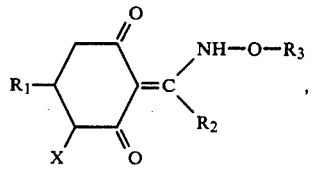

where $R_1$ is cyclohexenyl or cyclohexadienyl, X is hydrogen or alkoxycarbonyl, $R_2$ is alkyl and $R_3$ is alkyl, alkenyl, propargyl or haloalkenyl, and salts thereof, and herbicides containing these compounds.

6 Claims, No Drawings

CYCLOHEXANE-1,3-DIONE DERIVATIVES

This is a continuation of application Ser. No. 296,584, filed Aug. 27, 1981, abandoned.

The present invention relates to cyclohexane-1,3-dione derivatives, to the preparation of these compounds and to herbicides containing the compounds.

It is known that cyclohexane-1,3-dione derivatives, eg. the sodium salt of 2-(1-allyloxyaminobutylidene)-4-methoxycarbonyl-5,5-dimethylcyclohexane-1,3-dione (German Laid-Open Application DOS No. 2,439,104), 2-(1-ethoxyaminobutylidene)-5-(2-ethylthiopropyl)-cyclohexane-1,3-dione (German Laid-Open Application DOS No. 2,822,304) and 2-(1-allyloxyaminobutylidene)-5-cyclohexyl-cyclohexane-1,3-dione (Japanese Preliminary Published application 54/019,945), can be used as herbicides which are principally active against grassy weeds and grassy crop plants. At the same time, they are very well tolerated by broad-leaved crop plants.

We have found that compounds of the general formula I

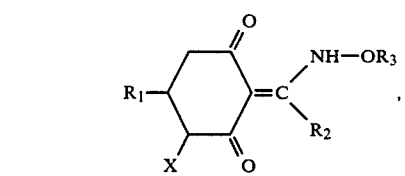

where $R_1$ is cyclohexenyl or cyclohexadienyl which is unsubstituted or substituted by from 1 to 5 alkyl groups, X is hydrogen or alkoxycarbonyl, where alkoxy is of 1 or 2 carbon atoms, $R_2$ is alkyl of 1 to 5 carbon atoms and $R_3$ is alkyl of 1 to 4 carbon atoms, alkenyl of 3 or 4 carbon atoms, propargyl or haloalkenyl of 3 or 4 carbon atoms and 1 to 3 halogen atoms, and the salts thereof, have a powerful herbicidal action on grasses and cause little or no damage, either to broad-leaved crops and non-gramineous monocotyledonous crops or, surprisingly, to some grassy crops, such as cereals and rice.

The novel compounds can exist in several tautomeric forms:

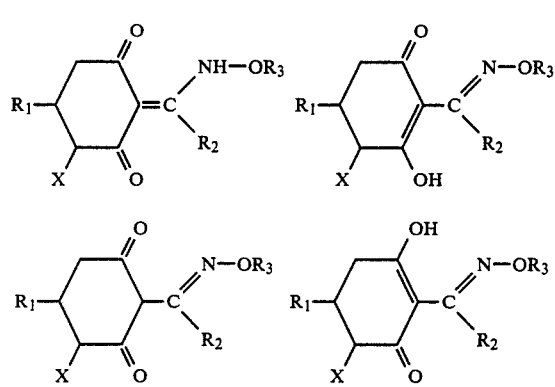

and can be obtained according to the following equation:

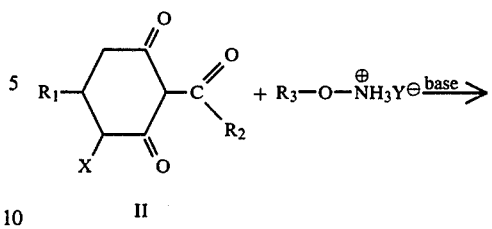

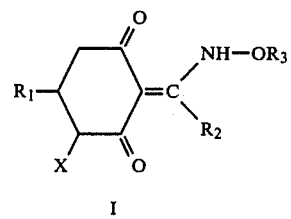

where $R^1$, $R^2$, $R^3$ and X have the above meanings and Y is an anion.

The reaction is advantageously carried out in a heterogeneous phase system in an inert solvent at from 0° to 80° C. or at the boiling point of the mixture, in the presence of a base, for example a carbonate, bicarbonate, acetate, alcoholate, hydroxide or oxide of an alkali metal or alkaline earth metal, in particular of sodium or potassium or of magnesium or calcium, or an organic base, such as pyridine or a tertiary amine.

The particularly suitable pH range for the reaction is from 2 to 7, in particular from 4.5 to 5.5. This range is advantageously obtained by adding acetates, for example those of alkali metals, in particular of sodium or potassium, or mixtures thereof, for example in amounts of from 0.5 to 2 moles, per mole of the ammonium compound.

Examples of suitable solvents are methanol, ethanol, isopropanol, benzene, tetrahydrofuran, chloroform, acetonitrile, dichloroethane, ethyl acetate, dioxane and dimethylsulfoxide.

The reaction is complete after a few hours, and the product can be isolated by concentrating the mixture, adding water and extracting the mixture with a nonpolar solvent, or by distilling off the solvent under reduced pressure.

The novel compounds can also be prepared by reacting a compound II with the corresponding amine $R_3$—$ONH_2$.

The compounds of the formula II can be obtained by acylating the cyclohexane-1,3-diones III, as described, for example, in Tetrahedron Letters 29, 2491:

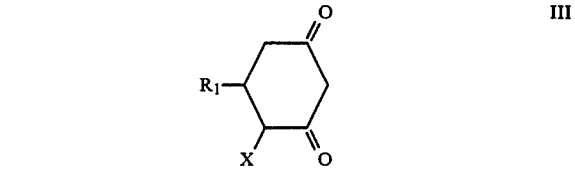

Compounds of the formula III can furthermore exist in the following tautomeric forms IIIa and IIIb:

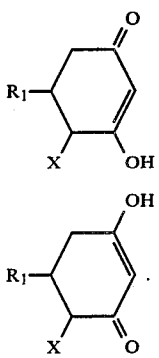

The compounds III can be prepared from aldehydes R₁CHO by methods known from the literature, for example by aldol condensation with acetone and subsequent cyclization with malonates by a method similar to that in Organic Synthesis, Coll. Volume II, page 200. The intermediates of the formula III are also obtained by subjecting the aldehyde R₁CHO to a Knoevenagel-Doebner reaction with malonic acid (cf. Org. Reactions, Volume 15, page 204), esterifying the acid formed and cyclizing the esterification product with an acetoacetate by a method similar to that described, for example, in Chem. Ber., 96, 2946.

In cases where $R_1$ is 1,3,3-trimethylcyclohex-1-en-2-yl or 2,4,4-trimethylcyclohex-1-en-3-yl, the readily accessible compounds α- or β-ionone-are advantageously used as the starting materials, as described in Chemical Abstracts 72, 111,408.

Examples of $R_1$ are cyclohex-1-en-4-yl, cyclohex-1-en-3-yl, cyclohex-1-en-1-yl, 5-methylcyclohex-1-en-4-yl, 1-methylcyclohex-1-en-2-yl, 1,3-dimethylcyclohex-1-en-2-yl, 3,5-dimethylcyclohex-1-en-4-yl, 3,6-dimethylcyclohex-1-en-4-yl, 3,3-dimethylcyclohex-1-en-2-yl, 1,3,3-trimethylcyclohex-1-en-2-yl, 2,4,4-trimethylcyclohex-1-en-3-yl, 3,5,6-trimethylcyclohex-1-en-4-yl, 3,5,5-trimethylcyclohex-1-en-4-yl, 3,3,5-trimethylcyclohex-1-en-4-yl, 1,5,5-trimethylcyclohexa-1,3-dien-4-yl, 4,6,6-trimethylcyclohexa-1,3-dien-5-yl, 2,6,6-trimethylcyclohexa-1,3-dien-1-yl, 1,2,3,5-trimethylcyclohex-1-en-4-yl, 1,3,3,4-tetramethylcyclohex-1-en-2-yl, 2,4,4,5-tetramethylcyclohex-1-en-3-yl and 3,5,5,6-tetramethylcyclohex-1-en-4-yl.

$R_2$ can be methyl, ethyl, n-propyl, i-propyl, n-butyl, sec.-butyl, i-butyl, tert.-butyl or straight-chain or branched pentyl.

Examples of $R_3$ are methyl, ethyl, n-propyl, i-propyl, n-butyl, sec.-butyl, i-butyl, tert.-butyl, allyl, propargyl, 1-chloroprop-1-en-3-yl, 2-chloroprop-1-en-3-yl, 1,2-dichloroprop-1-en-3-yl and 1,1,2-trichloroprop-1-en-3-yl.

X can be hydrogen, methoxycarbonyl or ethoxycarbonyl.

Examples of the salts of the compounds are those of the alkali metals, in particular of potassium or sodium, and these can be obtained by treating the compounds with sodium hydroxide or potassium hydroxide in aqueous solution or in an organic solvent, such as methanol, ethanol or acetone. Sodium alcoholates and potassium alcoholates can also be used as the base in this reaction.

Other metal salts, for example those of manganese, copper, zinc, iron and barium, can be prepared from the sodium salt by reaction with the corresponding metal chlorides in aqueous solution.

The examples which follow, in which parts by weight bear the same relation to parts by volume as that of the kilogram to the liter, illustrate the preparation of the novel cyclohexane-1,3-diones.

EXAMPLE 1

3.5 parts by weight of 2-butyryl-5-(cyclohex-1-en-4-yl)-cyclohexane-1,3-dione are dissolved in 100 parts by volume of ethanol, and 1.5 parts by weight of allyloxyammonium chloride and 1.2 parts by weight of anhydrous sodium acetate are added. The mixture is stirred at room temperature for 16 hours, the solvent is distilled off under reduced pressure, the residue is stirred with 50 parts by volume of water and 50 parts by volume of methylene chloride, the organic phase is separated off and the aqueous phase is extracted with 50 parts by volume of methylene chloride. The combined organic phases are washed with water, dried over sodium sulfate and concentrated under reduced pressure.

3.5 parts by weight of 2-(1-allyloxyaminobutylidene)-5-(cyclohex-1-en-4-yl)-cyclohexane-1,3-dione are obtained as an oil having the following structural formula (active ingredient No.1):

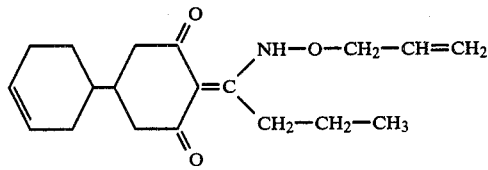

$C_{19}H_{27}NO_3$ (Molecular weight 317):
Calculated: C, 71.9; H, 8.6; N, 4.4; Found: C, 71.6; H, 8.8; N, 4.2.

EXAMPLE 2

8.0 parts by weight of 2-butyryl-5-(1,3,3-trimethylcyclohex-1-en-2-yl)-cyclohexane-1,3-dione are reacted with 2.9 parts by weight of allyloxyammonium chloride and 2.4 parts by weight of sodium acetate in 100 parts by volume of ethanol and the mixture is worked up, by a procedure similar to that of Example 1. 9.0 parts by weight of 2-(1-allyloxyaminobutylidene)-5-(1,3,3-trimethylcyclohex-1-en-2-yl)-cyclohexane-1,3-dione are obtained as a viscous oil (active ingredient No.2).

$C_{22}H_{33}NO_3$ (Molecular weight 360):
Calculated: C, 73.5; H, 9.2; N, 3.9; Found: C, 73.2; H, 9.1; N, 3.9.

EXAMPLE 3

9.0 parts by weight of 2-butyryl-4-carbomethoxy-5-(1,3,3-trimethylcyclohex-1-en-2-yl)-cyclohexane-1,3-dione are dissolved in 100 parts by volume of ethanol, and 1.5 parts by weight of ethoxyamine are added. The mixture is stirred at room temperature for 8 hours and concentrated under reduced pressure. The residue is taken up in 50 parts by volume of methylene chloride and the solution is washed with 5% strength hydrochloric acid and water and concentrated under reduced pressure. 2-(1-Ethoxyaminobutylidene)-4-carbomethoxy-5-(1,3,3-trimethylcyclohex-1-en-2-yl)-cyclohexane-1,3-dione is obtained in quantitative yield, as crystals of melting point 70° C. (active ingredient No.3).

The following compounds are obtained analogously:

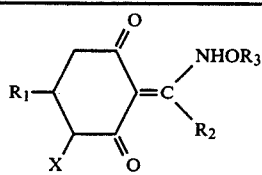 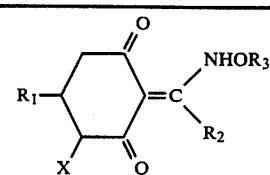

| No. | R₁ | R₂ | R₃ | X |
|---|---|---|---|---|
| 4 | Cyclohex-1-en-4-yl | n-C₃H₇ | —CH₂—CH=CH₂ | COOCH₃ |
| 5 | Cyclohex-1-en-4-yl | " | —C₂H₅ | COOCH₃ |
| 6 | Cyclohex-1-en-4-yl | " | " | H |
| 7 | 5-Methyl-cyclohex-1-en-4-yl | " | —CH₂—CH=CH₂ | COOCH₃ |
| 8 | 5-Methyl-cyclohex-1-en-4-yl | " | —C₂H₅ | COOCH₃ |
| 9 | 5-Methyl-cyclohex-1-en-4-yl | " | —CH₂—CH=CH₂ | H |
| 10 | 5-Methyl-cyclohex-1-en-4-yl | " | —C₂H₅ | H |
| 11 | 1,3,3-Trimethyl-cyclohex-1-en-2-yl | " | —CH₂—CH=CH₂ | COOCH₃ |
| 12 | 1,3,3-Trimethyl-cyclohex-1-en-2-yl | " | —C₂H₅ | H |
| 13 | 1,3,3-Trimethyl-cyclohex-1-en-2-yl | " | n-C₃H₇ | H |
| 14 | 1,3,3-Trimethyl-cyclohex-1-en-2-yl | " | —CH₂—C≡CH | H |
| 15 | 1,3,3-Trimethyl-cyclohex-1-en-2-yl | —C₂H₅ | —CH₂—CH=CH₂ | H |
| 16 | 1,3,3-Trimethyl-cyclohex-1-en-2-yl | " | —C₂H₅ | H |
| 17 | 2,4,4-Trimethyl-cyclohex-1-en-3-yl | n-C₃H₇ | —CH₂—CH=CH₂ | COOCH₃ |
| 18 | 2,4,4-Trimethyl-cyclohex-1-en-3-yl | " | —C₂H₅ | COOCH₃ |
| 19 | 2,4,4-Trimethyl-cyclohex-1-en-3-yl | " | —CH₂—CH=CH₂ | H |
| 20 | 2,4,4-Trimethyl-cyclohex-1-en-3-yl | " | —C₂H₅ | H |
| 21 | 1,5,5-Trimethyl-cyclohexan-1,3-dien-4-yl | " | —CH₂—CH=CH₂ | COOCH₃ |
| 22 | 1,5,5-Trimethyl-cyclohexan-1,3-dien-4-yl | " | —C₂H₅ | COOCH₃ |
| 23 | 1,5,5-Trimethyl-cyclohexan-1,3-dien-4-yl | " | —CH₂—CH=CH₂ | H |
| 24 | 1,5,5-Trimethyl-cyclohexan-1,3-dien-4-yl | " | —C₂H₅ | H |
| 25 | 1,3,3-Trimethyl-cyclohex-1-en-2-yl | " | —CH₂—CCl=CCl₂ | H |
| 26 | 1,3,3-Trimethyl-cyclohex-1-en-2-yl | " | —CH₂—CCl=CH₂ | H |
| 27 | 1,3,3-Trimethyl-cyclohex-1-en-2-yl | " | —CH₂—CH=CHCl | H |
| 28 | 2,4,4,5-Tetra-methyl-cyclohex-1-en-3-yl | " | C₂H₅ | H |
| 29 | 2,4,4,5-Tetra-methyl-cyclohex-1-en-3-yl | " | —CH₂—CH=CH₂ | H |
| 30 | 1,3,3,4-Tetra-methyl-cyclohex-1-en-2-yl | " | C₂H₅ | COOCH₃ |
| 31 | 1,3,3,4-Tetra-methyl-cyclohex-1-en-2-yl | " | —CH₂—CH=CH₂ | COOCH₃ |
| 32 | 1,3,3,4-Tetra-methyl-cyclohex-1-en-2-yl | " | C₂H₅ | H |
| 33 | 1,3,3,4-Tetra-methyl-cyclohex-1-en-2-yl | " | —CH₂—CH=CH₂ | H |
| 34 | 1,3,3-Tri-methyl-cyclohex-1-en-2-yl | n-C₄H₉ | C₂H₅ | H |
| 35 | 1,3,3-Tri-methyl-cyclohex-1-en-2-yl | " | —CH₂—CH=CH₂ | H |
| 36 | 1,3,3-Trimethyl-cyclohex-1-en-2-yl sodium salt | C₃H₇ | " | H |
| 37 | 1,3,3-Trimethyl-cyclohex-1-en-2-yl copper salt | " | " | H |
| 38 | 1-Methyl-cyclohex-1-en-4-yl | " | C₂H₅ | H |
| 39 | 1-Methyl-cyclohex-1-en-4-yl | " | —CH₂—CH=CH₂ | H |

-continued

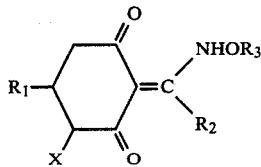

| No. | R₁ | R₂ | R₃ | X |
|---|---|---|---|---|
| 40 | 1-Methyl-cyclohex-1-en-4-yl | C₂H₅ | C₂H₅ | H |
| 41 | 1-Methyl-cyclohex-1-en-4-yl | " | —CH₂—CH=CH₂ | H |
| 42 | 1-Methyl-cyclohex-1-en-4-yl | C₃H₇ | —CH₂—CH=CHCl | H |
| 43 | 5-Methyl-cyclohex-1-en-4-yl | C₂H₅ | C₂H₅ | H |
| 44 | 5-Methyl-cyclohex-1-en-4-yl | " | —CH₂—CH=CH₂ | H |
| 45 | 5-Methyl-cyclohex-1-en-4-yl | C₃H₇ | —CH₂—CH=CHCl | H |
| 46 | 1,2-Dimethyl-cyclohex-1-en-4-yl | " | C₂H₅ | H |
| 47 | 1,2-Dimethyl-cyclohex-1-en-4-yl | " | —CH₂—CH=CH₂ | H |
| 48 | 1,2-Dimethyl-cyclohex-1-en-4-yl | n-C₃H₇ | —CH₂—CH=CHCl | H |
| 49 | 1,2-Dimethyl-cyclohex-1-en-4-yl | C₂H₅ | C₂H₅ | H |
| 50 | 1,2-Dimethyl-cyclohex-1-en-4-yl | " | —CH₂—CH=CH₂ | H |
| 51 | 1,5-Dimethyl-cyclohex-1-en-4-yl | " | C₂H₅ | H |
| 52 | 1,5-Dimethyl-cyclohex-1-en-4-yl | " | —CH₂—CH=CH₂ | H |
| 53 | 1,5-Dimethyl-cyclohex-1-en-4-yl | C₃H₇ | C₂H₅ | H |
| 54 | 1,5-Dimethyl-cyclohex-1-en-4-yl | " | —CH₂—CH=CH₂ | H |
| 55 | 1,5-Dimethyl-cyclohex-1-en-4-yl | " | —CH₂—CH=CH—Cl | H |
| 56 | 2,5-Dimethyl-cyclohex-1-en-4-yl | " | C₂H₅ | H |
| 57 | 2,5-Dimethyl-cyclohexen-1-yl | " | —CH₂—CH=CH₂ | H |
| 58 | 2,5-Dimethyl-cyclohexen-1-yl | " | —CH₂—CH=CHCl | H |
| 59 | 2,5-Dimethyl-cyclohexen-1-yl | " | C₂H₅ | H |
| 60 | 1,1,3-Trimethyl-cyclohex-1-en-2-yl | " | CH₃ | H |
| 61 | 1,1,3-Trimethyl-cyclohex-1-en-2-yl | C₂H₅ | —CH₂—CH=CHCl | H |
| 62 | 1,1,3-Trimethyl-cyclohex-1-en-2-yl | CH₃ | C₂H₅ | H |
| 63 | 1,1,3-Trimethyl-cyclohex-1-en-2-yl | " | —CH₂—CH=CH₂ | H |
| 64 | 2,4,4-Trimethyl-cyclohex-1-en-3-yl | C₂H₅ | C₂H₅ | H |
| 65 | 2,4,4-Trimethyl-cyclohex-1-en-3-yl | " | —CH₂—CH=CH₂ | H |
| 66 | 2,4,4-Trimethyl-cyclohex-1-en-3-yl | " | —CH₂—CH=CHCl | H |
| 67 | 1,3,3-Trimethyl-cyclohex-1-en-2-yl | " | CH₃ | H |
| 68 | 1,3,3-Trimethyl-cyclohex-1-en-3-yl | " | C₂H₅ | COOCH₃ |

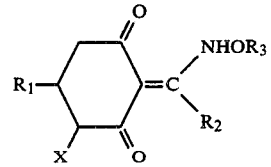

The ¹H—NMR spectroscopic data obtained with these compounds are given in the table below. The chemical shifts are related to tetramethylsilane as internal standard and given in δ values (ppm). The abbreviations have the following meanings: s=singlet, d=doublet, t=triplet, and q=quartet.

| Compound/active ingredient no. | Characteristic signals | | |
|---|---|---|---|
| | oxime ether moiety —O—CH₂— | 5-cyclohexenyl moiety | |
| | | H—C=C—H or | CH₃—C=C |
| 1 | 4.50, d | 5.65, s | |
| 2 | 4.55, d | | 1.70, s |
| 3 | 4.15, q | | 1.75, s |
| 4 | 4.53, d | 5.65, s | |
| 5 | 4.10, q | 5.65, s | |
| 6 | 4.10, q | 5.70, s | |
| 7 | 4.55, d | 5.70, s | |
| 8 | 4.05, q | 5.57, s | |
| 9 | 4.50, d | 5.60, s | |
| 10 | 4.10, q | 5.60, s | |
| 11 | 4.55, d | | 1.75, s |
| 12 | 4.05, q | | 1.70, s |
| 13 | 3.95, t | | 1.70, s |
| 14 | 4.55, d | | 1.70, s |
| 15 | 4.55, d | | 1.70, s |

-continued

| Compound/ active ingredient no. | Characteristic signals | | |
|---|---|---|---|
| | oxime ether moiety —O—CH$_2$— | 5-cyclohexenyl moiety H—C=C—H or CH$_3$—C=C | |
| 16 | 4.15, q | | 1.72, s |
| 17 | 4.55, d | | 1.80, s |
| 18 | 4.10, q | | 1.70, s |
| 19 | 4.55, d | | 1.70, s |
| 20 | 4.05, q | | 1.70, s |
| 21 | 4.55, d | | 1.75, s |
| 22 | 4.10, q | | 1.75, s |
| 23 | 4.50, d | | 1.75, s |
| 24 | 4.10, q | | 1.75, s |
| 25 | 4.80, s | | 1.70, s |
| 26 | 4.60, s | | 1.75, s |
| 27 | 4.55, q | | 1.68, s |
| 28 | 4.05, q | | 1.70, s |
| 29 | 4.45, d | | 1.70, s |
| 30 | 4.10, q | | 1.80, s |
| 31 | 4.56, d | | 1.78, s |
| 32 | 4.10, q | | 1.70, s |
| 33 | 4.55, d | | 1.73, s |
| 34 | 4.10, q | | 1.70, s |
| 35 | 4.50, d | | 1.70, s |
| 38 | 4.10, q | 5.38, m | 1.68, s |
| 39 | 4.50, d | 5.35, m | 1.65, s |
| 40 | 4.05, q | 5.30, m | 1.63, s |
| 41 | 4.50, d | 5.32, m | 1.63, s |
| 42 | 4.70, d, 4.40, d | 5.35, m | 1.65, s |
| 43 | 4.51, q | 5.60, m | |
| 44 | 4.52, d | 5.60, m | |
| 45 | 4.65, d, 4.35, d | 5.60, m | |
| 46 | 4.05, q | | 1.60, s |
| 47 | 4.50, d | | 1.63, s |
| 48 | 4.65, d, 4.40, d | | 1.60, s |
| 49 | 4.10, q | | 1.60, s |
| 50 | 4.55, d | | 1.65, s |
| 53 | 4.05, q | | |
| 54 | 4.50, d | | 1.63, s |
| 55 | 4.70, d, 4.35, d | | 1.60, s |
| 57 | 4.45, d | | 1.63, s |
| 58 | 4.70, d, 4.40, d | | 1.60, s |
| 59 | 4.10, q | | |
| 60 | 3.80, s | | 1.70, s |
| 61 | 4.70, d, 4.35 d | | 1.65 |
| 62 | 4.10, q | | 1.70 |
| 63 | 4.50, d | | 1.70 |
| 64 | 4.10, q | | 1.70 |
| 65 | 4.50, q | | 1.70 |
| 66 | 4.65, d, 4.40, d | | 1.70 |
| 67 | 3.80, s | | 1.72, s |
| 68 | 4.10, q | 5.55, s | 1.80, s |

The active ingredients may be applied as such, in the form of formulations, or application forms prepared therefrom, e.g., as directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible. The agents generally contain from 0.1 to 95, especially 10 to 80% (wt%) of active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

EXAMPLE I 90 parts by weight of compound 1 is mixed with 10 parts by weight of N-methyl-α-pyrrolidone. A mixture is obtained which is suitable for application in the form of very fine drops.

EXAMPLE II 10 parts by weight of compound 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE III 20 parts by weight of compound 2 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE IV 20 parts by weight of compound 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil.

EXAMPLE V 80 parts by weight of compound 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE VI 5 parts by weight of compound 1 is intimately mixed with 95 parts by weight of particulate kaolin. A dust is obtained containing 5% by weight of the active ingredient.

EXAMPLE VII 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE VIII 40 parts by weight of compound 1 is intimately mixed with 10 parts of the sodium salt of a phenolsulfonic acid-urea-formaldehyde condensate, 2 parts of silica gel and 48 parts of water. A stable aqueous dispersion is obtained.

EXAMPLE IX 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The influence of various representatives of the novel cyclohexane-1,3-dione derivatives on the growth of unwanted and crop plants is demonstrated in greenhouse experiments.

The vessels employed were plastic flowerpots having a volume of 300 cm$^3$, and which were filled with a sandy loam containing about 1.5% humus. In the case of Glycine max. and Oryza sativa, peat was added to ensure better growth. The seeds of the test plants were sown shallow, and separately, according to species.

For the postemergence treatment described here, the test plants were first grown to a height of from 3 to 15 cm, depending on growth form. The active ingredients were then applied for example at a rate of 0.125 kg/ha. The active ingredients were suspended or emulsified in water as vehicle, and sprayed through finely distributing nozzles.

The agents used for comparison purposes were:

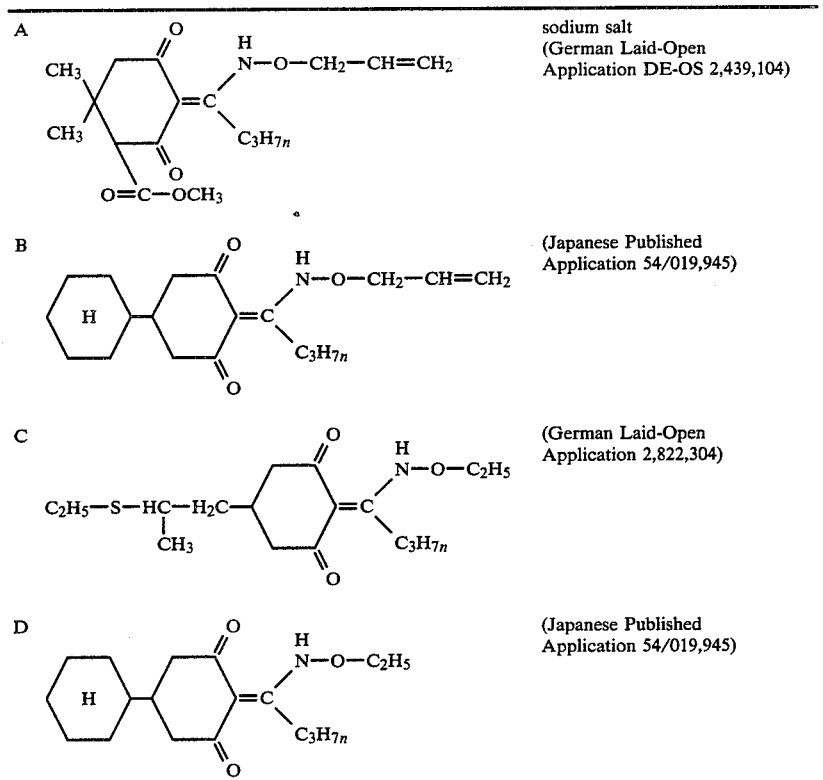

TABLE 1

| | List of plant names | |
|---|---|---|
| Botanical name | Abbreviation in Table | Common name |
| *Alopecurus myosuroides* | Alopec. myos. | blackgrass |
| *Beta vulgaris* | Beta vulg. | sugarbeets |
| *Digitaria sanguinalis* | Digit. sang. | large crabgrass |

TABLE 1-continued

| | List of plant names | |
|---|---|---|
| Botanical name | Abbreviation in Table | Common name |
| Glycine max | — | soybeans |
| Leptochloa spp. | Leptochl. spp. | sprangletop spp. |
| Oryza sativa | Oryza sat. | rice |
| Sorghum halepense | Sorgh. halep. | johnsongrass |
| Triticum aestivum | Tritic. aest. | wheat |
| Gossypium hirsutum | — | cotton |

The experiments were run in the greenhouse—species from warmer areas were set up at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The results show that the novel compounds according to the invention are suitable for combating grasses in cereals and rice and are at the same time excellently tolerated by broadleaved crops.

In an experiment to test herbicidal effectiveness on postemergence treatment in the greenhouse, novel compound 2 exhibited, at a rate of 0.125 kg/ha, better control of unwanted grasses than comparative agents A and B, but a slightly weaker action than comparative agent C. However, the tolerance by rice and wheat of novel compound 2 was much better than that of all 3 comparative agents A, B and C.

In an experiment to combat unwanted grasses on postemergence treatment, active ingredients 1 and 6 according to the invention had, at a rate of 0.125 g/ha, a better herbicidal action than comparative agent D, and were tolerated significantly better by the crop plant rice.

Experiments were also carried out (postemergence treatment) to determine the herbicidal action of compounds Nos. 12, 15, 19, 20 and 27 and their tolerance by crop plants. Prior art comparative agents B and D were compared directly with each other.

In these greenhouse experiments, compounds nos. 12, 15, 19, 20 and 27 proved to have on average, a similar herbicidal action on unwanted grasses to that of prior art comparative agent B and a stronger herbicidal action than D. All the active ingredients are tolerated well by broadleaved crop plants. However, what is decisive is that the prior art comparative agents B and D cause heavy damage to cereals, e.g., winter wheat, whereas the novel compounds have a selective action in such crops.

All the novel compounds given here by way of example are also selective in the broadleaved crops beets and soybeans.

If certain crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

In view of the good tolerance of the active ingredients and the many application methods possible, the agents according to the invention, or mixtures containing them, may be used not only on the crop plants listed in Table 1, but also in a much larger range of crops for removing unwanted plants. Application rates may vary from 0.1 to 15 kg/ha and more.

The following crop plants may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |

-continued

| Botanical name | Common name |
| --- | --- |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel cyclohexane-1,3-dione deivatives may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-$\alpha,\alpha,\beta,\beta$-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-$\beta$-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-($\beta$-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiocarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate 3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methylα-chloro-β-(4-chlorophenyl)-propionate
methylα,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methylpropyen-2-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloroacetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide 2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)

2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts esters) gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl 4-[4-(4'-trifluoromethyl)-phenoxy]-pentene-2-carboxylate 2-chloro-4-trifluoromethyl-3'-methoxycarbonyl-4'-nitrophenyl ether
2,4-dichlorophenyl-3'-carboxy-4'-nitrophenyl ether (salts)
4,5-dimethoxy-2-(3-α,α,β-triflfuoro-β-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1(3-chloro-4-ethoxyphenyl)-3,3-dimethylurea
ethyl 2-methyl-4-chlorophenoxy-thioacetate
2-chloro-3,5-diiodo-4-acetoxy-yiridine
1(-4-[2-(4-methylphenyl)-ethoxy]-phenyl-3-methyl-3-methoxyurea
2,6-dimethyl-N-(pyrazol-1-yl-methylenoxymethyl)-2-chloroacetanilide
2-methyl-6-ethyl-N-(pyrazol-1-yl-methylenoxymethyl)-2-chloroacetanilide
2-methyl-6-ethyl-N-(pyrazol-1-yl-methylenoxymethyl)-2-chloroacetanilide
1-(α-2,4-dichlorophenoxypropionic acid)-3-(O-methylcarbamoyl)-anilide
1-(α-2-bromo-4-chlorophenoxypropionic acid)-3-(O-methylcarbamoyl)-anilide.

We claim:

1. A cyclohexane-1,3-dione derivative of the formula

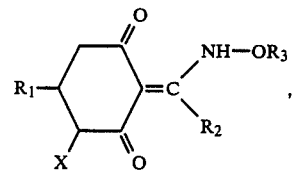

where $R_1$ is cyclohexenyl or cyclohexadienyl which is unsubstituted or substituted by from 1 to 5 alkyl groups, X is hydrogen, $R_2$ is alkyl of 1 to 5 carbon atoms and $R_3$ is alkyl of 1 to 4 carbon atoms, alkenyl of 3 or 4 carbon atoms, propargyl or haloalkenyl of 3 or 4 carbon atoms and 1 to 3 halogen atoms, and the salts thereof.

2. A process for combating unwanted plants, wherein the plants or the soil are treated with an effective amount of a cyclohexane-1,3-dione derivative of the formula

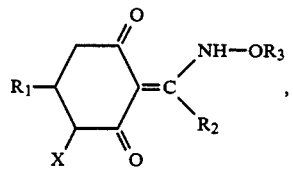

where $R_1$ is cyclohexenyl or cyclohexadienyl which is unsubstituted or substituted by from 1 to 5 alkyl groups, X is hydrogen, $R_2$ is alkyl of 1 to 5 carbon atoms and $R_3$ is alkyl of 1 to 4 carbon atoms, alkenyl of 3 or 4 carbon atoms, propargyl or haloalkenyl of 3 or 4 carbon atoms and 1 to 3 halogen atoms, or a salt thereof.

3. 2-(1-Allyloxyaminobutylidene)-5-(1,3,3-trimethyl-cyclohex-1-en-2-yl)-cyclohexane-1,3-dione.

4. A process for combating unwanted plants, wherein the plants or the soil are treated with an effective amount of the compound of claim 3.

5. A compound of the formula I as defined in claim 1, wherein $R_1$ is cyclohexenyl or cyclohexadienyl which is unsubstituted or substituted by from 1 to 4 methyl groups, X is hydrogen, $R_2$ is ethyl or propyl, and $R_3$ is ethyl, allyl or chloroallyl, and the salts thereof.

6. A process for combating unwanted plants, wherein the plants or the soil are treated with an effective amount of a compound of the formula I as defined in claim 5.

* * * * *